United States Patent
Knauf et al.

(10) Patent No.: US 10,125,090 B2
(45) Date of Patent: Nov. 13, 2018

(54) PROCESS FOR PREPARATION OF DI- AND POLYAMINES OF THE DIPHENYLMETHANE SERIES

(71) Applicant: Covestro Deutschland AG, Leverkusen (DE)

(72) Inventors: Thomas Knauf, Dormagen (DE); Stefan Wershofen, Mönchengladbach (DE); Klaus-Gerd Gruner, Duisburg (DE); Volker Hartjes, Duisburg (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 15/317,301

(22) PCT Filed: Jun. 22, 2015

(86) PCT No.: PCT/EP2015/063922
§ 371 (c)(1),
(2) Date: Dec. 8, 2016

(87) PCT Pub. No.: WO2015/197519
PCT Pub. Date: Dec. 30, 2015

(65) Prior Publication Data
US 2017/0114000 A1     Apr. 27, 2017

(30) Foreign Application Priority Data

Jun. 24, 2014  (EP) .................................... 14173581

(51) Int. Cl.
*C07C 209/78*     (2006.01)
*C08G 73/02*      (2006.01)
*C07C 211/50*     (2006.01)

(52) U.S. Cl.
CPC ........ *C07C 209/78* (2013.01); *C08G 73/0266* (2013.01)

(58) Field of Classification Search
CPC ........................... C08G 73/00; C08G 73/0266
USPC ......................................................... 528/269
See application file for complete search history.

(56) References Cited

U.S. PATENT DOCUMENTS

| | | | |
|---|---|---|---|
| 4,792,624 A | 12/1988 | Hatfield, Jr. et al. |
| 5,053,539 A | 10/1991 | Yano et al. |
| 5,286,760 A | 2/1994 | Bolton et al. |
| 6,433,219 B1 | 8/2002 | Ströfer et al. |
| 6,576,788 B1 | 6/2003 | Penzel et al. |
| 6,649,798 B2 | 11/2003 | Klein et al. |
| 6,831,192 B2 | 12/2004 | Ströfer et al. |
| 7,186,857 B2 | 3/2007 | Müller et al. |
| 7,230,130 B2 | 6/2007 | Ströfer et al. |
| 7,253,321 B2 | 8/2007 | Hagen et al. |

(Continued)

FOREIGN PATENT DOCUMENTS

| DE | 844896 | 9/1952 |
|---|---|---|
| GB | 1517585 | 7/1978 |

OTHER PUBLICATIONS

Treybal, Robert E.; Mass-Transfer Operations; Third Edition; 1980; McGraw-Hill Book Co.; pp. 477-541.

(Continued)

*Primary Examiner* — Duc Truong
(74) *Attorney, Agent, or Firm* — Donald R. Palladino

(57) ABSTRACT

The invention relates to a method for the preparation of di- and polyamines of the diphenylmethane series, care being taken during the shutdown of the production process that an excess of aniline and respect to formalin is ensured.

10 Claims, 2 Drawing Sheets

(56) References Cited

U.S. PATENT DOCUMENTS

| | | |
|---|---|---|
| 7,312,362 B2 | 12/2007 | Keggenhoff et al. |
| 7,528,283 B2 | 5/2009 | Pohl et al. |
| 9,138,717 B2 | 9/2015 | Ding et al. |
| 2009/0240077 A1 | 9/2009 | Wershofen et al. |

OTHER PUBLICATIONS

Twitchett, H. J.; Chemical Society reviews; 1974; 3(2); "Chemistry of the Production of Organic Isocyanates"; pp. 209-230.
Kirk-Othmer Encyclopedia of Chemical Technology (see "http://onlinelibrary.wiley.com/book/10.1002/0471238967"); John Wiley & Sons, Inc.; Extraction, Liquid-Liquid; pp. 22-23 (mixer-settler cascades or settling vessels); published online: Jun. 15, 2007.
Müller, E. et al; Ullmann's Encyclopedia of Industrial Chemistry; "Liquid-Liquid Extraction"; vol. 21; pp. 272-274; 2012 Wiley VCH Verlag GmbH & Co. KGaA, Weinheim, DOI: 10.1002/14356007.b03_06.pub2.

PROCESS FOR PREPARATION OF DI- AND POLYAMINES OF THE DIPHENYLMETHANE SERIES

CROSS-REFERENCE TO RELATED APPLICATIONS

This application is a National Phase Application of PCT/EP2015/063922, filed Jun. 22, 2015, which claims priority to European Application No. 14173581.1, filed Jun. 24, 2014, each of which being incorporated herein by reference.

FIELD

The invention relates to a process for preparing diamines and polyamines of the diphenylmethane series, in which care is taken during the running-down of the production process that an excess of aniline over formalin is ensured.

BACKGROUND

The continuous or partially discontinuous preparation of MDA is disclosed in, for example, EP 1 616 890 A1, U.S. Pat. No. 5,286,760, EP-A-451442 and WO-A-99/40059. The acidic concentration of aromatic amines and formaldehyde to form diamines and polyamines of the diphenylmethane series proceeds in a plurality of reaction steps.

In the aminal process, formaldehyde is firstly condensed with aniline in the absence of an acid catalyst to form aminal, with water being eliminated. The rearrangement to form MDA is then carried out in the presence of an acid catalyst in a first step to form para- and ortho-aminobenzylaniline. The aminobenzylanilines rearrange in a second step to form MDA. Main products of the acid-catalyzed reaction of aniline and formaldehyde are the diamine 4,4'-MDA, its positional isomers 2,4'-MDA and 2,2'-MDA and also higher homologs.

In the neutralization process, aniline and formaldehyde are converted directly in the presence of an acid catalyst into aminobenzylanilines which subsequently react further to form the two-ring MDA isomers and MDA homologs having more than two rings.

Regardless of the process variant for preparing the acidic reaction mixture, the work-up of this is, according to the prior art, commenced by neutralization by means of a base. The neutralization is usually carried out at temperatures of, for example, from 90° C. to 100° C. without addition of further substances. (H. J. Twitchett, Chem. Soc. Rev. 3(2), 223 (1974)). However, it can also be carried out at a different temperature level, for example in order to accelerate the degradation of interfering by-products. Hydroxides of the alkali and alkaline earth elements are suitable as bases. Preference is given to using aqueous NaOH.

After neutralization, the organic phase is separated from the aqueous phase in a separation vessel. The organic phase containing crude MDA which remains after the aqueous phase has been separated off is subjected to further work-up steps, for example, a wash with water (base wash) in order to wash residual salts out from the crude MDA. The crude MDA which has been purified in this way is finally freed of excess aniline, water, and other materials (e.g. further solvents) present in the mixture by suitable processes such as distillation, extraction or crystallization. The work-up which is routine according to the prior art is disclosed, for example, in EP 1 652 835 A1, page 3, line 58 to page 4, line 13, or EP 2 103 595 A1, page 7, lines 21 to 37.

EP 2 486 975 A1 discloses the use of a specific mixer-reactor in the preparation of MDA. It is stated that a local excess of formaldehyde can lead to the formation of network-like polymers. However, the patent application gives no details about the configuration of the reaction running-down procedure, i.e. interruption of the process. In particular, the patent application does not teach that the "A/F ratio" (the molar ratio of aniline to formaldehyde) during the running-down procedure should be above the A/F ratio during normal operation.

EP 1 616 890 A1 teaches that aniline and formaldehyde are firstly reacted in the absence of the acid catalyst to form aminal and the aminal is subsequently admixed with an acid catalyst and is reacted further at temperatures of from 20° C. to 100° C. and at water contents of the acidic reaction mixture obtained in this way of from 0 to 20% by weight. In particular, the water is firstly at least partly removed from the aminal after condensation of formaldehyde and aniline to form aminal, with a water content of from 0 to 5% by weight in the aminal being set, and the aminal is subsequently admixed with an acid catalyst and is reacted further at temperatures of from 20° C. to 100° C. and water contents of the acidic reaction mixture obtained in this way of from 0 to 20% by weight. Mixtures of diamines and polyamines of the diphenylmethane series having degrees of protonation of <15%, preferably from 4% to 14%, particularly preferably from 5% to 13%, can be prepared in this way. Here, the degree of protonation is, in the case of monoprotic acid catalysts (e.g. hydrochloric acid), the molar ratio of the amount of acid catalyst used and the molar amount of amine functions present in the reaction mixture. The patent application does not given any details regarding the procedure during running-down of an industrial production plant. The examples gives are laboratory experiments. In particular, this patent application does not teach that the A/F ratio during the running-down procedure should be above the A/F ratio during normal operation.

EP 0 283 757 A1 is likewise concerned with the preparation of MDA. The process described is characterized by the addition of aniline-free MDAs to aminobenzylamines formed by condensation of aniline and formaldehyde before the rearrangement reaction of these induced by heat. Example 2 describes a mode of operation in which a small part of the MDA formed is recirculated to the rearrangement reaction (cf. also claim 8). In other words: the configuration of an MDA plant in continuous normal operation is described. Details of the procedure when running-down an MDA plant are not described; in particular, there is no information about the A/F ratio during running-down compared to the A/F ratio during the reaction.

WO-A-99/40059 teaches that, in order to prepare methylenedi(phenylamine) by reaction of aniline with formaldehyde in the presence of acid catalysts in a semicontinous process, aniline and optionally acid catalyst are initially charged, formaldehyde and optionally acid catalyst are fed through a mixing device into a circuit in which aniline, optionally acid catalyst and optionally previously introduced formaldehyde are circulated, and the reaction mixture is brought to a temperature of greater than 75° C. after introduction of at least 50% of the total amount of formaldehyde to be fed in. The addition up to an amount of at least 50% of the total amount of formaldehyde to be fed in is carried out at a temperature of the reaction mixture in the circuit of from 20° C. to 75° C.

None of the above-mentioned document of the prior art suggests using a A/F ratio which differs from that during normal operation during running-down of the reaction for preparing MDA. It is thus quite routine in the prior art to use A/F ratios during normal operation which are above that conforming to the stoichiometry of the reaction (2:1). However, the prior art does not in any way suggest maintaining even greater A/F ratios during running-down.

The quality of a process for preparing MDA is defined firstly by the content of undesirable by-products of the reaction in the product. Secondly, the quality of a process is defined by the overall process from start-up, normal production to running-down of the process being able to be operated without technical failure of production or problems which require intervention in the process and by there being no losses of starting materials, intermediates or end product.

Such problems can, for example occur during taking the aminal reaction out of operation (during "running-down"). Such problems can, for example, be that there is formation of high molecular weight solids which lead to caking and blockages on the equipment (aminal vessel, aminal cooler and aminal separator and conduits).

Although the above-described processes of the prior art are able to produce MDA in high yield without a reduction in quality of the end products, only processes which are in normal operation are described. Running-down processes until stoppage of the plant is attained (known as "running-down time") are not taken into account.

Start-up and running-down times frequently occur in everyday industrial operation and are not necessarily associated with opening or other mechanical intervention in a reactor or other apparatus of the plant, but can also be associated with shutting-down and restarting of the production plant for various other reasons, e.g. lack of raw materials. These running-down times are in practice characterized in that deviations in the desired molar ratio of aniline to formalin can occur.

SUMMARY

It would therefore be desirable to have an improved process for preparing diamines and polyamines of the diphenylmethane series, in which attention is paid to the period of time during which the reaction is run down. It is an object of the present invention to provide such a process.

This object is achieved according to the invention by a process for preparing diamines and polyamines of the diphenylmethane series (MDA) by reaction of aniline (1) and formaldehyde (2) at a molar ratio of aniline (1) to formaldehyde (2) in normal operation of A/F$_{normal\ operation}$, which preferably has a value of from 1.5 to 20, particularly preferably from 1.5 to 15, very particularly preferably from 1.5 to 10 and very especially preferably from 1.5 to 6, which comprises the steps:

Either, according to a variant A)
A.I) Reaction of aniline (1) and formaldehyde (2) in the absence of an acid catalyst (3) in a reactor to form an aminal, where aniline (1) is introduced at a mass flow rate m$_1$ and formaldehyde is introduced at a mass flow rate m$_2$ into the reactor and the resulting reaction mixture is subsequently separated into an aqueous phase and an organic, aminal-containing phase;
A.II) Reaction of at least part of the organic, aminal-containing phase obtained in step I) with acid (3) in a reactor, with the aminal reacting to form diamines and polyamines of the diphenylmethane series;
wherein the following steps are carried out to end the production of the diamines and polyamines of the diphenylmethane series:

A.I.1) reduction of the mass flow rate m$_2$ of the formaldehyde (2) into the reactor of step A.I), commencing at a point in time t$_0$, until m$_2$ is zero at a point in time t$_1$, where t$_1$>t$_0$;
A.I.2) reduction of the mass flow rate m$_1$ of the aniline into the reactor of step A.I) until m$_1$ is zero at a point in time t$_2$, where t$_2$≥t$_1$;
A.II.1) reduction of the mass flow rate m$_3$ of acid (3), until m$_3$ zero;
and
the reduction of the mass flow rates m$_1$ and m$_2$ occurs in such a way that, up to attainment of the point in time t$_1$, the instantaneous molar ratio of
aniline (1) introduced into the reactor of step A.I)
to
formaldehyde (2) introduced into the reactor of step A.I), A/F$_{inst.}$, is always ≥1.5, preferably ≥2, where A/F$_{inst.}$ in all embodiments is always ≥1.05·A/F$_{normal\ operation}$ up to attainment of the point in time t$_1$;
or, according to a variant B),
B.I) reaction of aniline (1) and acid (3) in a reactor to form a reaction mixture containing the anilinium salt of the acid (3) used;
B.II) reaction of at least part of the reaction mixture obtained in step B.I) with formaldehyde (2) in a reactor, optionally with introduction of further aniline (1), optionally with the introduction of further acid (3), forming diamines and polyamines of the diphenylmethane series;
wherein the following steps are carried out to end the production of the diamines and polyamines of the diphenylmethane series:
B.II.1) reduction of the mass flow rate m$_2$ of formaldehyde (2) into the reactor of step B.II) commencing at a point in time t$_0$, until m$_2$ is zero at a point in time t$_1$, where t$_1$>t$_0$;
B.I.1) reduction of the mass flow rate m$_1$ of aniline into the reactor of step B.I) and optionally into the reactor of step B.II), until m$_1$ is zero at a point in time t$_2$, where t$_2$≥t$_1$;
B.I.2) reduction of the mass flow rate m$_3$ of the acid (3) into the reactor of step B.I) and optionally into the reactor of step B.II), until m$_3$ is zero;
and
the reduction of the mass flow rates m$_1$ and m$_2$ occurs in such a way that, up to attainment of the point in time t$_1$, the instantaneous molar ratio of
aniline (1) introduced into the reactor of step B.I) and, if present, aniline (1) introduced into the reactor of step B.II)
to
formaldehyde (2) introduced into the reactor of step B.II), A/F$_{inst.}$, is always ≥1.5, preferably ≥2, where A/F$_{inst.}$ in all embodiments is particularly preferably always ≥1.05·A/F$_{normal\ operation}$ up to attainment of the point in time t$_1$.

DETAILED DESCRIPTION

Figure 1:
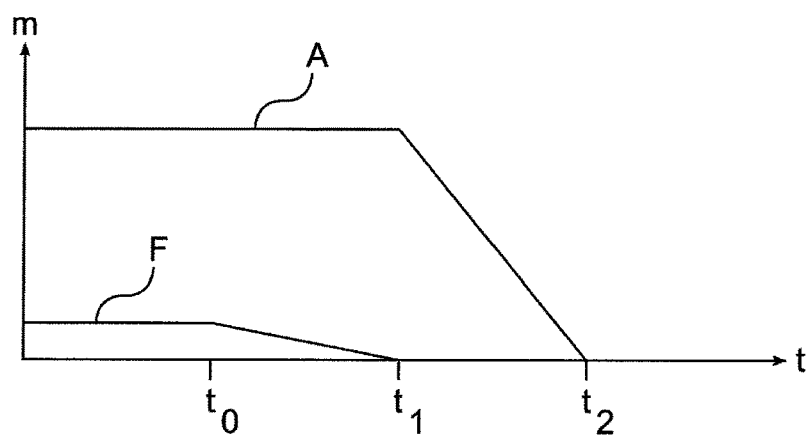
FIG. 1 shows the course over time of the mass flow rates of aniline and formaldehyde in an embodiment according to variant A) of the process of the invention.

The running-down procedure can proceed from a state of full load, partial load or the minimum load specific to the plant concerned. Regardless of the prevailing load, the state from which the running-down procedure is commenced at the point in time $t_0$ is, for the purposes of the present invention, referred to as normal operation.

For the purposes of the present invention, diamines and polyamines of the diphenylmethane series are amines and mixtures of amines of the following type:

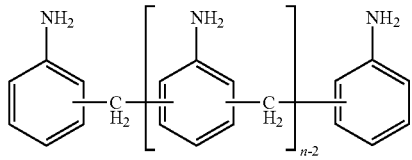

Here, n is a natural number of $\geq 2$. In the following, the compounds of this type in which n=2 will also be referred to as diamines of the diphenylmethane series or diaminodiphenylmethanes (hereinafter MMDA). Compounds of this type in which n>2 will for the purposes of the present invention also be referred to as polyamines of the diphenylmethane series or polyphenylenepolymethylenepolyamine (hereinafter PMDA). Mixtures of the two types will also be referred to as diamines and polyamines of the diphenylmethane series (hereinafter MDA). Industrially, the diamine and polyamine mixtures are predominantly converted by phosgenation into the corresponding diisocyanates and polyisocyanates of the diphenylmethane series.

In both variants, the reactors of steps I) and II) can be identical or different. This means that in variant A) it is equally possible for the aminal formed in step A.I) to be left in the reactor and the acid to be added or for the aminal to be transferred into another reactor and the acid (3) then to be added there. In variant B), it is equally possible for the reaction product of aniline (1) and acid (3) formed in step B.I) to be left in the reactor and the formaldehyde (2) to be added or for the reaction product of aniline (1) and acid (3) to be transferred to another reactor and the formaldehyde (2) then to be added there. Furthermore, the term "a reactor" also encompasses, for the purposes of the present invention, the case that a reactor cascade is used (in other words the word "a" is in this context to be interpreted as the indefinite article and not as an indication of number).

In both variants, the steps I) and II) are carried out continuously or semicontinuously, preferably continuously.

The instantaneous molar ratio, $A/F_{inst.}$, in the period of time up to $t_1$ can in the case of variant A) be derived in a simple manner from the known feed streams (1) and (2) into the reactor of step A.I) at a particular point in time t. In the case of variant B), the instantaneous molar ratio, $A/F_{inst.}$, in the period of time up to $t_1$ can be derived in an analogous way from the known feed streams (1) and (2) into the reactor of step B.I) or into the reactor of step B.II) at a particular point in time t. If use is made of the possibility of introducing further aniline into the reactor of step B.II) in step B.II), this is, for the purpose of determining the instantaneous molar ratio, $A/F_{inst.}$, added during the period of time up to $t_1$ to the aniline of step B.I). If such aniline added in step B.II) is mixed beforehand with acid so that it is present as anilinium salt, this does not change the calculation since one mole of aniline reacts with one mole of acid to form one mole of anilinium salt. For the purposes of calculating the instantaneous molar ratio $A/F_{inst.}$, the calculation can be carried out as if all aniline (1) were present in free form.

For the purposes of the invention, the reduction of the mass flow rates $m_1$ and $m_2$ (for example expressed in kg of feed aniline/hour and kg of formaldehyde/hour or kg formaldehyde solution/hour) is carried out in such a way that $A/F_{inst.}$ is always $\geq 1.5$, preferably $\geq 2$, until the point in time $t_1$ has been attained, with $A/F_{inst.}$ particularly preferably being $\geq 1.05 \cdot A/F_{normal\ operation}$ up to attainment of the point in time $t_1$ in all embodiments. For theoretical reasons, this does not apply at the point in time $t_1$ itself since the mass flow rate $m_2$ of the formaldehyde is then zero. In any case, however, the reduction of the formaldehyde input is carried out in such a way that at least the stoichiometric amount of aniline required for formation of MDA is present in the respective reactor during the running-down procedure.

In both variants, the introduction of formaldehyde into the respective reactor is, preferably steplessly, throttled back to zero during the period of time from $t_0$ to $t_1$ in the first step of the running-down procedure (step A.I.1) or B.II.1)), while the introduction of aniline continues to run at the same load, a greater load or a reduced load. This allows complete reaction of the formaldehyde present in the reactor of step A.I) or B.II) and discharge of the product formed from this reactor until, in variant A, virtually only aniline is present in the aminal reactor and the apparatuses of the further process steps, or, in variant B, virtually only aniline is present in the reactor of step B.II) and in the apparatuses of the further process steps.

In the second step of the running-down procedure (step A.I.1) or B.I.1)), the introduction of aniline is finally stopped.

In the third step of the running-down procedure (step A.II.1) or B.I.2)), the introduction of acid is stopped. In both variants, the mass flow rate $m_3$ of acid (3) is preferably reduced commencing at the earliest at the point in time $t_1$. In both variants, particular preference is given to maintaining the mass flow rate $m_3$ prevailing at the commencement of the running-down procedure (i.e. before steps A.I.1) or B.II.1)) are carried out) up to the point in time $t_2$ and then starting the introduction of further acid (3) (for example by carefully closing a valve), so that any residual amounts of acid (3) remaining in the feed conduits continue to be fed in for a certain time. This ensures that sufficiently large amounts of salt are present in the subsequent work-up (neutralization), which make phase separation easier.

Embodiments of the process of the invention are described below. They can be combined with one another in any way, unless the contrary is clear from the context.

During the running-down procedure, the reaction temperature in the reactor space of the reactor of step A.I) is, for example, from 20° C. to 120° C., preferably from 40° C. to 110° C. and very preferably from 60° C. to 100° C., in the case of variant A). The reactor of step A.I) (aminal reactor) is operated at atmospheric pressure or at superatmospheric pressure. Preference is given to a pressure of from 1.05 to 5 bar absolute, very particularly preferably from 1.1 to 3 bar and very particularly preferably from 1.2 bar to 2 bar absolute, prevailing. The pressure is maintained by means of pressure regulating valves or by connecting the offgas systems of the aminal reactor and the overflow of the aminal separator. The aminal separator and the outflow of the aqueous phase are preferably heated in order to prevent caking.

In the case of variant B), the reaction temperature in the reactor space of the reactor of step B.II) is, for example, from 20° C. to 200° C. and preferably from 20° C. to 160° C. during the running-down procedure. Before running-down, the temperature is >75° C., and the temperature decreases during running-down if the reactor is not heated.

After running-down, the apparatuses with aniline still present therein can be allowed to stand. As an alternative, one apparatus, more than one apparatus or all apparatuses can be emptied, for example in order to prepare them for maintenance measures.

According to the invention, the reduction of the mass flow rates $m_1$ and $m_2$ (for example expressed in kg of feed aniline/hour and kg of formaldehyde/hour or kg of formaldehyde solution/hour) in steps I.1) and I.2) is carried out in such a way that the molar ratio of aniline to formaldehyde in the first reactor is ≥2:1 up to attainment of the point in time $t_1$. For theoretical reasons, this does not apply at the point in time $t_1$ itself since the mass flow rate $m_2$ of the formaldehyde is then zero. However, the reduction in the formaldehyde input is in any case carried out so that at least the stoichiometric amount of aniline required for formation of MDA is present in the reactor.

If two or more MDA reactor lines are to be operated in parallel, it is possible for one reactor line firstly to be run down and the other reactor lines to be run down in succession, but this does not have to be the case. It is also possible to run down all MDA reactor lines close to simultaneously.

In a further embodiment of the process of the invention, the mixture obtained is also discharged from the reactor during and/or after step A.I) or B.II). As a result, the production process including the participating transport of materials can be continued. The discharge is advantageously continued until, in variant A, virtually only aniline is present in the aminal reactor and in the apparatuses of the further process steps or, in variant B, virtually only aniline is present in the reactor of step B.II) and in the apparatuses of the further process steps.

In a further embodiment of the process of the invention, $t_2-t_1>0$ hour in both variants A) and B). This period of time is preferably from >0 hour to <30 hours, more preferably from >0.5 hour to <10 hours and very particularly preferably from >1 hour to <5 hours.

In a further embodiment of the process of the invention, the mass flow rate $m_1$ is ≥1000 kg/hour in both variants A) and B). This mass flow rate is preferably from ≥2000 kg/hour to ≤200 000 kg/hour, more preferably from ≥3000 kg/hour to ≤100 000 kg/hour.

In a further embodiment of the process of the invention, the mass flow rate $m_2$ is ≥300 kg/hour in step I) and in step II) in both variants A) and B). This mass flow rate is preferably from ≥400 kg/hour to ≤100 000 kg/hour, more preferably from ≥500 kg/hour to ≤50 000 kg/hour.

The formaldehyde (2) used can in both variants originate from all known production processes for formaldehyde. Mention will merely be made by way of example of the silver catalyst process.

In a further embodiment of the process of the invention, at least the reactor of step A.I) or of step B.I) is, in both variants A) and B), at least partly filled with aniline after the point in time $t_2$; i.e. aniline (or anilinium salt) still present in the respective reactor after ending of the introduction of aniline is not completely discharged. When aniline (or anilinium salt) remains in the respective reactor without the presence of formaldehyde, production can be interrupted without formation of undesirable high molecular weight by-products.

The ways in which the process is carried out in the variants A) and B) in normal operation up to the point at which the crude product is obtained are described in more detail below:

The preparation of diamines and/or polyamines of the diphenylmethane series according to variant A) can be summarized by way of example as follows:

a) key procedure of step I): aniline and formaldehyde are condensed in the absence of an acid catalyst to form aminal and water and the resulting aminal is discharged from the aminal reactor, and b) water from step a), which originates mainly from water of condensation of the aminal reaction and water from the starting material formaldehyde, is at least partly separated off as an aqueous phase from the reaction mixture from the aminal reaction, and c) key procedure of step II): the aminal from step b) is rearranged in the presence of an acid catalyst to form MDA.

The condensation of aniline and formaldehyde in step a) can be carried out by any method according to the prior art. Here, aniline and aqueous formaldehyde solution are normally condensed in molar ratios in the range from 1.5 to 20, preferably from 1.5 to 15, particularly preferably from 1.5 to 10 and very particularly preferably from 1.5 to 6, at temperatures of from 20° C. to 120° C., preferably from 40° C. to 110° C. and particularly preferably from 60° C. to 100° C., to form aminal and water. The reaction is usually carried out at atmospheric pressure. Suitable aniline grades are, for example, described in EP 1 257 522 B1, EP 2 103 595 A1 and EP 1 813 598 B1. Preference is given to using technical grades of formalin (aqueous solution of formaldehyde) containing from 30% by mass to 50% by mass of formaldehyde in water. However, formaldehyde solutions having lower or higher concentrations or the use of gaseous formaldehyde are also conceivable.

In step b), organic aminal phase and aqueous phase are separated at temperatures of from 20° C. to 120° C., preferably from 40° C. to 110° C., particularly preferably from 60° C. to 100° C., preferably at ambient pressure. The phase separation can also be carried out at slightly superatmospheric pressure.

The rearrangement of the aminal in step c) is carried out in the presence of an acid catalysts usually a strong mineral acid such as hydrochloric acid. Preference is given to using mineral acid in a molar ratio of mineral acid to aniline of from 0.001 to 0.9, preferably from 0.05 to 0.5. It is naturally also possible to use solid, acid catalysts as described in the literature. Here, formaldehyde can be introduced into a mixture of aniline and acid catalyst and the reaction solution can be reacted to completion by stepwise heating. As an alternative, aniline and formaldehyde can also firstly be prereacted and subsequently admixed, with or without prior removal of water, with the acid catalyst or a mixture of further aniline and acid catalyst, after which the reaction solution is reacted to completion by stepwise heating. This reaction can be carried out continuously or batchwise by one of the numerous methods described in the literature (e.g. in EP 1 616 890 A1 or EP 127 0544 A1).

The preparation of the crude diamines and/or polyamines of the diphenylmethane series according to variant B) can be summarized by way of example as follows:
a) key procedure of step B.I): aniline and acid are reacted in the absence of formaldehyde to form a reaction mixture containing the anilinium salt of the acid used, and
b) key procedure of step B.II): the reaction mixture from step a), which contains the anilinium salt of the acid used, is admixed with formaldehyde and rearranged to form MDA.

The reaction of aniline and acid, preferably hydrochloric acid, in step a) can be carried out by a method according to the prior art. The further description will be given for the example of aqueous hydrochloric acid, but other acids can also be used. Aniline and an aqueous hydrochloric acid are normally reacted at molar ratios of aniline to acid in the range from 1.6 to 100, preferably from 3.3 to 20. This reaction can be carried out in an upstream reactor or a mixing section, with the reaction mixture optionally being able to be temporarily stored in a stock vessel. This reaction can optionally be carried out in the same reactor in which the subsequent reaction of the reaction mixture of aniline and acid with formaldehyde takes place. Suitable aniline grades are, for example, described in EP 1 257 522 B1, EP 2 103 595 A1 and EP 1 813 598 B1. Suitable hydrochloric acid grades are, for example, described in EP 1 652 835 A1.

"Feed aniline" can firstly be placed in the reactor at temperatures of from 10° C. to 60° C. The feed aniline is made up of fresh aniline and optionally aniline from the MDA distillation (described in more detail further below; see step h)) and optionally aniline from the wastewater treatment.

Then, for example while the introduction of aniline is proceeding, the hydrochloric acid is introduced into the initially charged aniline, with care being taken to ensure good mixing. This good mixing can be achieved by stirring by means of a stirrer or by circulation (by means of pumps) of the reaction mixture or by a combination of stirring and circulation. The entire plant from feed streams to offtake of product should optionally be ready for operation. The reaction apparatus can, if necessary, be equipped with an internal or external heat exchanger in order to be able to remove the heat of reaction evolved. As an alternative, the feed aniline and/or the hydrochloric acid can also be appropriately cooled. A further alternative is the use of evaporative cooling for removing the heat of reaction.

In step b), the aniline hydrochloride-containing reaction mixture from step a) is reacted with aqueous formaldehyde solution. Here, formaldehyde can be introduced into a mixture of aniline and acid catalyst and the reaction solution can be reacted to completion by stepwise heating, as described, for example, in EP 1 053 222 A1. The reaction is usually carried out at temperatures of from 20° C. to 150° C.

The reactor of step B.I) and the reactor of step B.II) are advantageously different from one another. However, carrying out steps B.I) and B.II) in the same reactor is not ruled out. This reaction can be carried out continuously, semicontinuously or batchwise.

Preference is given to use technical grades of formalin (aqueous solution of formaldehyde) containing from 30% by mass to 50% by mass of formaldehyde in water. However, formaldehyde solutions having lower or higher concentrations or the use of gaseous formaldehyde are also conceivable.

In the case of a semicontinuous or batchwise reaction, an "infinite" excess of aniline in the form of free aniline and aniline hydrochloride is present at the point in time $t_1$ (=mass flow rate of formaldehyde equal to zero). From the point in time $t_0$ to attainment of the point in time $t_1$, formaldehyde is preferably introduced in such amounts that at least 1.05 times the $A/F_{normal\ operation}$ ratio provided in the formulation for normal operation is maintained.

In both variants A) and B), a crude reaction mixture containing diamines and polyamines of the diphenylmethane series is obtained (in variant A) in step c) and in variant B) in step b)). The work-up of this reaction mixture is preferably carried out as follows, regardless of whether variant A) or B) is employed:
d) the reaction mixture containing diamines and polyamines of the diphenylmethane series is neutralized, and
e) the neutralized reaction mixture containing diamines and polyamines of the diphenylmethane series is separated in a separation vessel into an organic phase containing diamines and polyamines of the diphenylmethane series and an aqueous phase, and
f) the organic phase containing diamines and polyamines of the diphenylmethane series is purified further by means of washing liquid in a washing vessel, and
g) the resulting mixture is separated in a separation vessel into an organic phase containing diamines and polyamines of the diphenylmethane series and an aqueous phase, and
h) the washed organic phase containing diamines and polyamines of the diphenylmethane series is freed of water and aniline by distillation.

In step d), the reaction mixture containing the diamines and polyamines of the diphenylmethane series is neutralized, optionally with addition of water and/or aniline. According to the prior art, the neutralization is usually carried out at temperatures of, for example, from 90° C. to 100° C. without addition of further substances. However, it can also be carried out at a different temperature level, for example in order to accelerate the degradation of interfering by-products. The hydroxides of the alkali elements and alkaline earth elements, for example, are suitable as bases. Aqueous NaOH is preferably employed. The base used for neutralization is preferably used in amounts of greater than 100%, particularly preferably from 105% to 120%, of the stoichiometrically required amount for neutralization of the acid catalyst used (see EP 1 652 835 A1).

The neutralized reaction mixture containing the diamines and polyamines of the diphenylmethane series is subsequently separated in step e) into an organic phase containing diamines and polyamines of the diphenylmethane series and an aqueous phase. This can be assisted by the addition of aniline and/or water. If the phase separation is assisted by addition of aniline and/or water, the addition of these/this is preferably carried out with intensive mixing as early as in the neutralization. Here, mixing can be effected in mixing sections having static mixers, in stirred vessels or cascades of stirred vessels or else in a combination of mixing sections and stirred vessels. The reaction mixture which has been neutralized and diluted by addition of aniline and/or water is then preferably fed into an apparatus which, owing to its configuration and/or internals, is particularly suitable for separation into an organic phase containing MDA and an aqueous phase, preferably phase separation or extraction apparatuses according to the prior art, as are described, for example, in Mass-Transfer Operations, 3rd Edition, 1980, McGraw-Hill Book Co, pp. 477 to 541, or Ullmann's Encyclopedia of Industrial Chemistry (Vol. 21, Liquid-Liquid Extraction, E. Müller et al., pages 272-274, 2012 Wiley-VCH Verlag GmbH & Co. KGaA, Weinheim, DOI: 10.1002/14356007.b03_06.pub2) or in Kirk-Othmer Encyclopedia of Chemical Technology (see "http://onlinelibrary.wiley.com/book/10.1002/0471238961", published online: Jun. 15, 2007, pages 22-23) (mixer-settler cascades or settling vessels).

Washing of the organic phase with water follows in step f), and renewed settling out of the water phase to remove residual contents of salt follows in step g) (preferably as described in DE-A-2549890, page 3).

In step h), water and aniline are separated off by distillation from the organic phase containing diamines and polyamines of the diphenylmethane series obtained in step g), as described in EP 1 813 597 B1. The organic phase obtained in step g) preferably has a composition, based on the weight of the mixture, of 5-15% by weight of water and, depending on the ratios of aniline and formaldehyde used, 5-90% by weight, preferably 5-40% by weight, of aniline and 5-90% by weight, preferably 50-90% by weight, of diamines and polyamines of the diphenylmethane series. After exit from the phase separation in step g), the organic phase containing diamines and polyamines of the diphenylmethane series usually has a temperature of 80° C.-150° C.

The resulting diamines and polyamines of the diphenylmethane series can be converted into the corresponding diisocyanates and polyisocyanates of the diphenylmethane series, viz MDI, by the known methods under inert conditions by reaction with phosgene in an organic solvent. Here, the phosgenation can be carried out by one of the methods known from the prior art (e.g. DE-A-844896 or DE-A-19817691).

If the above-mentioned conditions are adhered to during running-down, the following advantages are obtained:
i) avoidance of blockages and deposits in the aminal vessel, cooler, separator and the aminal cooling circulation pump and thus avoidance of a second start-up procedure because the plant does not have to be run down again and opened for the purpose of cleaning the equipment.
ii) saving of energy because the start-up procedure does not have to be carried out a second time because of the formation of blockages and deposits and the resulting shutdown of the plant for the purpose of cleaning the equipment.
iii) an increase in the productivity of the plant because the on-stream times of the reactor are increased because cleaning times for removing blockages and deposits are dispensed with.
iv) avoidance or reduction of precipitates, caked material and blockages in the equipment (aminal vessel, cooler, separator and the aminal cooling circulation pump) and, associated therewith, an increase in the operating time of the process.
v) reduced waste after cleaning the equipment (high molecular weight solids) and saving of incineration costs.
vi) avoidance of out-of-specification product which can be formed as a result of multiple poor starting up and running down: such poor-quality running-down product thus does not have to be blended with good-quality MDA or, in the worst case, even incinerated.
vii) better phase separation of aqueous and organic phases due to the absence of high molecular weight compounds which have an adverse effect on the phase separation.

The present invention is illustrated in detail with the aid of the following drawings and examples, but without being restricted thereto.

The drawings show:
FIG. 1-4 the course over time of the mass flow rates of aniline and formaldehyde in the process of the invention according to variant A)

FIG. 1 shows the course over time of the mass flow rates of aniline and formaldehyde in an embodiment according to variant A) of the process of the invention. The time t is plotted on the x axis and mass flow rates m are plotted on the Y axis. Until attainment of the point in time $t_0$, the mass flow rates for aniline ($m_1$, in the figure denoted by "A") and for formaldehyde ($m_2$, in the figure denoted by "F") into the aminal reactor designated in the terminology of the present invention as reactor of step A.I) are constant. It is now decided that the production needs to be run down. For this purpose, the mass flow rate of formaldehyde into the aminal reactor is reduced at an unchanged magnitude of the mass flow rate of aniline, until the mass flow rate of formaldehyde is zero at the point in time $t_1$.

At the point in time $t_1$, reduction of the mass flow rate of aniline into the aminal reactor is commenced, until it is likewise zero at the point in time $t_2$. It can be seen that the mass flow rate of aniline introduced into the aminal reactor is at least so much greater than the mass flow rate of formaldehyde that the molar ratio of aniline to formaldehyde is at least 2 at any point in time during running-down of the reaction.

During the time between $t_1$ and $t_2$, the formaldehyde still present in the aminal reactor can react to completion with the aniline. Finally, there can no longer be any free formaldehyde present in the aminal reactor.

It is of course possible in this variant for the reaction mixture obtained to continue to be discharged from the aminal reactor after the points in time $t_0$, $t_1$ and/or $t_2$.

Figure 2:
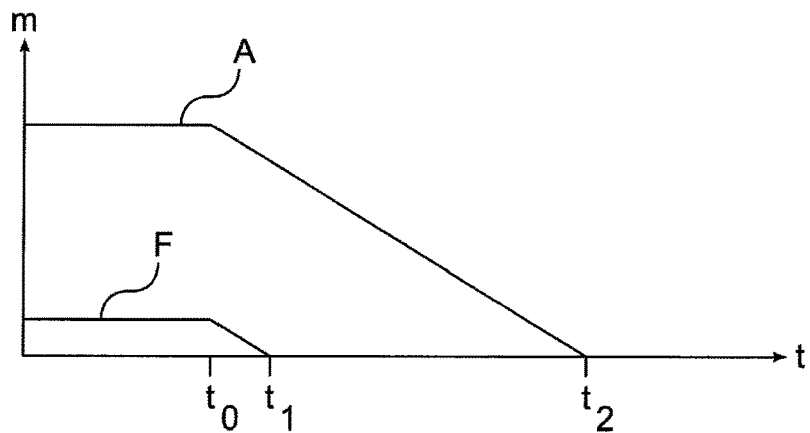
FIG. 2 shows, in a manner analogous to FIG. 1, the course over time of the mass flow rates of aniline and formaldehyde in a further embodiment according to variant A) of the process of the invention.

FIG. 2 shows, in a manner analogous to FIG. 1, the course over time of the mass flow rates of aniline and formaldehyde in a further embodiment according to variant A) of the process of the invention. Here, the mass flow rate of aniline is also reduced as early as the point in time $t_0$.

Figure 3:
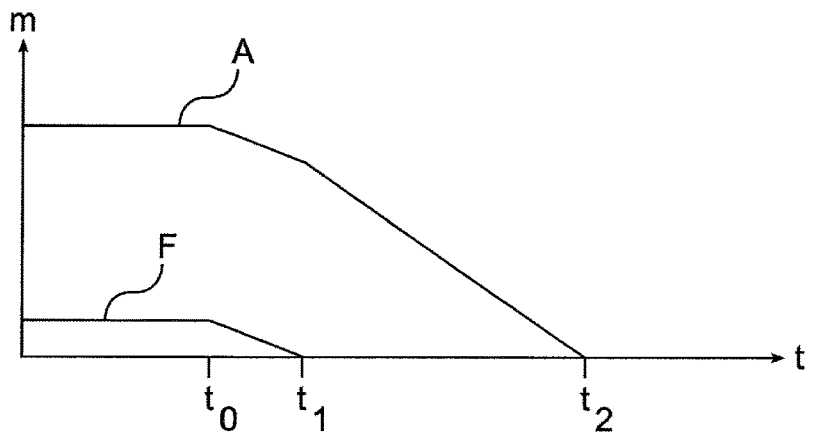
FIG. 3 shows, in a manner analogous to FIG. 2, the course over time of the mass flow rates of aniline and formaldehyde, with the introduction of aniline into the aminal reactor being reduced at two different speeds.

FIG. 3 shows, in a manner analogous to FIG. 2, the course over time of the mass flow rates of aniline and formaldehyde, with the introduction of aniline into the aminal reactor being reduced at two different speeds.

Figure 4:
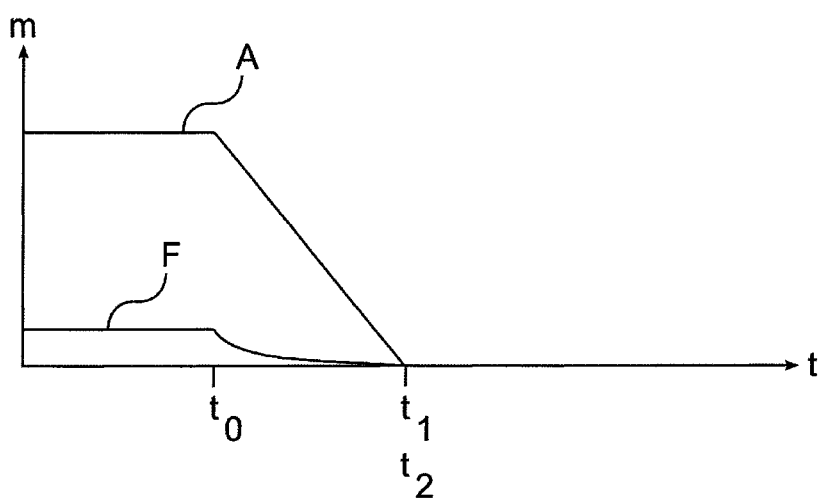
FIG. 4 depicts an embodiment of the variant A) in which both the introduction of aniline and the introduction of formaldehyde into the aminal reactor are reduced at the point in time $t_0$ and the reduction is selected in such a way that the introduction of the two reaction components into the aminal reactor is zero at the same point in time, while adhering to the boundary conditions according to the invention in respect of the molar ratio of aniline to formaldehyde.

FIG. 4 finally depicts an embodiment of the variant A) in which both the introduction of aniline and the introduction of formaldehyde into the aminal reactor are reduced at the point in time $t_0$ and the reduction is selected in such a way that the introduction of the two reaction components into the aminal reactor is zero at the same point in time, while adhering to the boundary conditions according to the invention in respect of the molar ratio of aniline to formaldehyde.

EXAMPLES

General Conditions for the Preparation of MDA in a Run-in Production Plant (Before Commencement of the Running-Down Procedure)

In a continuous reaction process (step a)), 24.3 t/h of feed aniline (containing 90% by mass of aniline) and 9.9 t/h of 32% strength aqueous formaldehyde solution (molar ratio of aniline to formalin 2.1:1) were mixed and reacted in a stirred reaction vessel at 90° C. and 1.4 bar absolute to form aminal. The reaction vessel was provided with a cooler having a cooling circulation pump. The reaction mixture leaving the reaction vessel was fed into a phase separation apparatus (aminal separator) (step b)).

After the phase separation to remove the aqueous phase, the organic phase was admixed in a mixing nozzle with 30% strength aqueous hydrochloric acid (degree of protonation 10%, i.e. 0.1 mol of HCl are added per mole of amino groups) and fed into the first rearrangement reactor. The rearrangement reaction was carried out at from 45° C. to 165° C. in a reactor cascade (step c)).

After the reaction was complete, the reaction mixture obtained was admixed with 32% strength sodium hydroxide solution in a molar ratio of sodium hydroxide to HCl of 1.1:1 and reacted in a stirred neutralization vessel (step d)). The temperature was 115° C. The absolute pressure was 1.4 bar. The neutralized reaction mixture was subsequently separated in a neutralization separator into a lower, aqueous phase, which is conveyed to a wastewater collection vessel, and an organic phase (step e)).

The upper, organic phase was conveyed to washing and washed with condensate in a stirred washing vessel (step f)). After the washing water had been separated off in a washing water separator (step g)), the crude MDA obtained in this way was freed of water and aniline by distillation, giving 17 t/h of MDA as bottom product (step h)).

Example 1 (Comparative Example): Running-Down of the MDA Plant, with Aniline being Stopped First The MDA plant was, as described in the general conditions for the preparation of MDA, operated at a load of 17 t/h of MDA. After a technical defect in the rearrangement reactors, aniline was stopped in the aminal reactor and formalin was stopped two minutes later. The addition of hydrochloric acid was interrupted at the same point in time as the addition of aniline. The aminal reactor and the rearrangement reactors were emptied. After the defect in the rearrangement reactors had been rectified, the empty aminal reactor was filled with feed aniline (containing 90% by mass of aniline) until aniline flowed over via the siphon into the aminal separator. When the aminal reactor had been filled to this extent, the feed aniline flowed at a rate of 12.2 t/h into the stirred aminal reaction vessel, which corresponded to 50% of the nominal load.

The formalin conduit was then opened. The reaction commenced immediately and the reaction mixture was regulated to 90° C. The pressure in the aminal reactor was 1.4 bar absolute during the start-up phase. The amount of 32% strength aqueous formaldehyde solution which was to be introduced into the aminal reactor during a planned start-up time t of 45 minutes should be increased steplessly from 0 t/h to 4.95 t/h, which corresponded to 50% of the nominal load. However, the plant had to be shut down after 30 minutes because the aminal vessel, the aminal cooler and the aminal separator were blocked and the aminal cooling circulation pump was likewise blocked with solid and did not operate.

Example 2 (Comparative Example): Running-Down of the MDA Plant, with the Introduction of Formalin and Aniline being Reduced Close to Simultaneously The MDA plant was, as described in the general conditions for the preparation of MDA, operated at a load of 17 t/h of MDA. After a technical defect in the aminal reactor, aniline and formaldehyde were stopped at essentially the same time. The addition of hydrochloric acid was interrupted at the same point in time as the addition of aniline.

The aminal reactor was emptied. After the defect had been rectified, the empty aminal reactor was filled with feed aniline (containing 90% by mass of aniline) until aniline flowed over via the siphon into the aminal separator. When the aminal reactor had been filled to this extent, the feed aniline flowed at a rate of 12.2 t/h into the stirred aminal reaction vessel, which corresponded to 50% of the nominal load.

The formalin conduit was then opened. The reaction commenced immediately and the reaction mixture was regulated to 90° C. The pressure in the aminal reactor was 1.4 bar absolute during the start-up phase. During a start-up time of 45 minutes, the amount of 32% strength aqueous formaldehyde solution introduced into the aminal reactor was increased steplessly from 0 t/h to 4.95 t/h. The reaction mixture was subsequently conveyed from the aminal reactor into a phase separation apparatus in which the water of reaction from the aminal reaction was separated off. The remaining organic phase was then pumped into the first rearrangement tank, with a 30% strength aqueous hydrochloric acid, corresponding to a degree of protonation of 10% (i.e. 0.1 mol of HCl are added per mole of amino groups) being introduced at the same time via a mixing nozzle into the inlet for the aminal into the first rearrangement tank.

The rearrangement reaction took place at from 50° C. to 150° C. in a reactor cascade (step c)). After the reaction was complete, the reaction mixture obtained was worked up as described in the general conditions for the preparation of MDA. After three production days, the aminal reactor had to be taken out of operation because solid had precipitated in the aminal separator and made cleaning necessary.

Example 3 (According to the Invention): Running-Down of the MDA Plant, with Further Aniline being Fed in The MDA plant was, as described in the general conditions for the preparation of MDA, operated at a load of 17 t/h of MDA. After a technical defect in the rearrangement reactors, formalin was stopped in the aminal reactor and aniline was stopped one hour later. The addition of hydrochloric acid was interrupted at the same point in time as the addition of aniline.

The aminal reactor and the rearrangement reactors were emptied. After the defect in the rearrangement reactors had been rectified, the empty aminal reactor was filled with feed aniline (containing 90% by mass of aniline) until aniline flowed over via the siphon into the aminal separator. When the aminal reactor had been filled to this extent, the feed aniline flowed at a rate of 12.2 t/h into the stirred aminal reaction vessel, which corresponded to 50% of the nominal load.

The formalin conduit was then opened. The reaction commenced immediately and the reaction mixture was regulated to 90° C. The pressure in the aminal reactor was 1.4 bar absolute during the start-up phase. During a start-up time of 45 minutes, the amount of 32% strength aqueous formaldehyde solution introduced into the aminal reactor was increased steplessly from 0 t/h to 4.95 t/h.

The reaction mixture was subsequently conveyed from the aminal reactor into a phase separation apparatus in which the water of reaction from the aminal reaction was separated off. The remaining organic phase was then pumped into the first rearrangement tank, with a 30% strength aqueous hydrochloric acid, corresponding to a degree of protonation of 10% (i.e. 0.1 mol of HCl are added per mole of amino groups), was introduced at the same time via a mixing nozzle into the inlet for the aminal into the first rearrangement tank. The rearrangement reaction took place at from 50° C. to 150° C. in a reactor cascade (step c)).

After the reaction was complete, the reaction mixture obtained was worked up as described in the general conditions for the preparation of MDA.

In the mode of operation according to the invention, the formation of deposits in the aminal vessel, in the aminal cooler and in the aminal separator, which can then grow further after the subsequent starting-up of the plant and during subsequent continuous operation and even after a short time cause blockages in the aminal vessel, in the aminal cooler, in the aminal separator and also stoppage of the cooling circulation pump due to solid deposits, was prevented during the running-down phase.

In the case of correct running-down of the plant and correct subsequent start-up of the plant, the aminal vessel could be operated without problems over a long production cycle of a number of months. The formation of undesirable by-products such as insoluble polymeric amines, etc., was significantly reduced and later blending of the start-up product with pure MDA or in the worst case incineration of the start-up product could be dispensed with.

The invention claimed is:

1. A process for preparing diamines and polyamines of the diphenylmethane series (MDA) by reaction of aniline (1) and formaldehyde (2) at a molar ratio of aniline (1) to formaldehyde (2) in normal operation of $A/F_{normal\ operation}$, which comprises the steps:
   A.I) reacting aniline (1) and formaldehyde (2) in the absence of an acid catalyst (3) in a reactor to form an aminal, where aniline (1) is introduced at a mass flow rate $m_1$ and formaldehyde (2) is introduced at a mass flow rate $m_2$ into the reactor and the resulting reaction mixture is subsequently separated into an aqueous phase and an organic, aminal-containing phase; and
   A.II) reacting at least part of the organic, aminal-containing phase obtained in step A.I) with acid (3) in a reactor, with the aminal reacting to form diamines and polyamines of the diphenylmethane series;
   wherein the following steps are carried out to end the production of the diamines and polyamines of the diphenylmethane series:
   A.I.1) reducing the mass flow rate $m_2$ of the formaldehyde (2) into the reactor of step A.I), commencing at a point in time $t_0$, until $m_2$ is zero at a point in time $t_1$, where $t_1 > t_0$;
   A.I.2) reducing the mass flow rate $m_1$ of the aniline into the reactor of step A.I) until $m_1$ is zero at a point in time $t_2$, where $t_2 \geq t_1$; and
   A.II.1) reducing the mass flow rate $m_3$ of acid (3), until $m_3$ zero;
   and
   the reduction of the mass flow rates $m_1$ and $m_2$ occurs in such a way that, up to attainment of the point in time $t_1$, the instantaneous molar ratio of
   aniline (1) introduced into the reactor of step A.I)
   to
   formaldehyde (2) introduced into the reactor of step A.I), $A/F_{inst.}$, is always $\geq 1.5$ and is always $\geq 1.05 \cdot A/F_{normal\ operation}$.

2. The process as claimed in claim 1, wherein the steps I) and II) are carried out in the form of a continuous process.

3. The process as claimed in claim 1, wherein the mixture obtained is also discharged from the respective reactor during and/or after step A.I).

4. The process as claimed in claim 1, wherein $t_2 - t_1$ is $>0$ hour.

5. The process as claimed in claim 1, wherein the mass flow rate $m_1$ is $\geq 1000$ kg/hour.

6. The process as claimed in claim 1, wherein the mass flow rate $m_2$ is $\geq 300$ kg/hour.

7. The process as claimed in claim 1, wherein at least the reactor of step A.I) is at least partly full of aniline after the point in time $t_2$.

8. The process as claimed in claim 1, wherein the mass flow rate $m_3$ of acid (3) is reduced at the earliest commencing at the point in time $t_1$.

9. The process as claimed in claim 8, wherein the mass flow rate $m_3$ prevailing before step A.I.1) is carried out is maintained up to the point in time $t_2$.

10. The process as claimed in claim 8, wherein the introduction of further acid (3) is stopped at the point in time $t_2$.

* * * * *